(12) United States Patent
Saitoh et al.

(10) Patent No.: US 7,988,309 B2
(45) Date of Patent: Aug. 2, 2011

(54) CORNER CUBE MEMBER ILLUMINATION DEVICE AND INSPECTION SYSTEM HAVING THE SAME

(75) Inventors: Kenji Saitoh, Atsugi (JP); Hiroshi Yoshikawa, Kawasaki (JP)

(73) Assignee: Canon Kabushiki Kaisha (JP)

( * ) Notice: Subject to any disclaimer, the term of this patent is extended or adjusted under 35 U.S.C. 154(b) by 235 days.

(21) Appl. No.: 11/863,649

(22) Filed: Sep. 28, 2007

(65) Prior Publication Data

US 2008/0080161 A1    Apr. 3, 2008

(30) Foreign Application Priority Data

Oct. 2, 2006 (JP) .................................. 2006-270652

(51) Int. Cl.
- G03B 15/02 (2006.01)
- G03B 15/06 (2006.01)
- F21V 7/05 (2006.01)

(52) U.S. Cl. ............... 362/3; 362/16; 362/297; 362/349
(58) Field of Classification Search ......... 362/3, 217.01, 362/297, 362, 16–18, 348; 396/4, 155, 200, 396/267
See application file for complete search history.

(56) References Cited

U.S. PATENT DOCUMENTS

| | | | |
|---|---|---|---|
| 3,267,278 A * | 8/1966 | Doolittle | 362/309 |
| 3,390,621 A * | 7/1968 | Land | 396/132 |
| 3,716,710 A * | 2/1973 | Clostermann et al. | 362/339 |
| 3,829,680 A * | 8/1974 | Jones | 362/330 |
| 4,355,350 A * | 10/1982 | Mader | 362/347 |
| 4,526,439 A * | 7/1985 | Okoshi et al. | 359/458 |
| 5,813,743 A | 9/1998 | Naka | |
| 5,946,134 A * | 8/1999 | Benson et al. | 359/529 |
| 6,058,271 A | 5/2000 | Tenmyo | |
| 6,082,885 A * | 7/2000 | Belfer | 362/554 |
| 6,086,227 A * | 7/2000 | O'Connell et al. | 362/297 |
| 6,335,724 B1 * | 1/2002 | Takekawa et al. | 345/173 |
| 6,634,759 B1 * | 10/2003 | Li | 359/853 |
| 6,952,202 B2 * | 10/2005 | Hirabayashi | 345/175 |
| 7,513,641 B2 * | 4/2009 | Nakano | 362/241 |
| 2004/0061689 A1 * | 4/2004 | Ito | 345/175 |
| 2005/0195599 A1 * | 9/2005 | Marka | 362/232 |
| 2008/0231976 A1 * | 9/2008 | Commander et al. | 359/833 |

FOREIGN PATENT DOCUMENTS

| | | |
|---|---|---|
| JP | 04-138438 | 5/1992 |
| JP | 08-234277 | 9/1996 |
| JP | 08-262537 | 10/1996 |
| JP | 2004-177523 | 6/2004 |

(Continued)

OTHER PUBLICATIONS

Stewart, James E.; Optical Principles and Technology for Engineers; CRC Press; p. 115; 1996.

(Continued)

*Primary Examiner* — Jong-Suk (James) Lee
*Assistant Examiner* — Stanley Weinberg
(74) *Attorney, Agent, or Firm* — Rossi, Kimms & McDowell LLP (57) ABSTRACT

An illumination device has a light source that supplies illumination light to an object to be illuminated and also has a corner cube member disposed at the opposite side of the light source with respect to the object to be illuminated. With this feature, efficient illumination of the object to be illuminated is achieved without need for high precision in positioning.

7 Claims, 12 Drawing Sheets

FOREIGN PATENT DOCUMENTS

JP          2005-086391         3/2005

OTHER PUBLICATIONS

Chandler, K.N., On effects of small errors in angles of corner-cube reflectors, Optical Society of America—Journal, v. 50, n. 3, pp. 203-206, Mar. 1960.

Downs, J.W.; Practical Conic Sections: The Geometric Properties of Ellipses, Parabolas and Hyperbolas;Courier Dover Publications; p. 66; 2003.

Vowinkel. B; The Main Beam Efficiency of Corner Cube Reflectors; International Journal of Infrared and Millimeter Waves; vol. 7, No. 1; 1986; West Germany.

Eckhardt, H.D.; Simple Model of Corner Reflector Phenomena; Applied Optics; vol. 10, No. 7; Jul. 1971; Burlington Massachusetts.

Gunawan; Devi S., et al.; Micromachined corner cube reflectors as a communication link; Sensors and Actuators, Department of Electrical Engineering University of California; pp. 580-583; 1995; Los Angeles CA.

Cooke, Frank; Making masters for corner cube reflectors, Optical Activities in Industry; Applied Optics; vol. 20, No. 8; pp. 1267-1268; Apr. 15, 1981; Brookfield Mass.

Kuo, In-Cheer, et al.; Laser resonators of a mirror and corner cube reflector: analysis by the imaging method; Institute of Science and Technology, Electronic Division; Applied Optics; vol. 23, No. 1; Jan. 1, 1984; Taiwan, China.

Steel, W.H.; How to represent a cube corner, Symbols Units Nomenclature; Applied Optics; vol. 22. No. 6; pp. 761-763; Mar. 15, 1983; Australia.

Schrijvershof, M.; Engineering Village; A quantitative description of the performance and shape of general corner cube reflectors; Proceedings of the SPIE—The International Society for Optical Engineering; Apr. 17-18 1986; USA.

Günter, Seeber et al.; Satellite Geodesy, Walter de Gruyter; p. 406 (2003).

World Survey of Current Research and Development on Roads and Road Transport; United States Federal Highway Administration, International Road Federation; p. 336 (1973).

* cited by examiner

CORNER CUBE MEMBER ILLUMINATION DEVICE AND INSPECTION SYSTEM HAVING THE SAME

BACKGROUND OF THE INVENTION

1. Field of the Invention

The present invention relates to an illumination device capable of efficiently illuminating an illumination area on an object to be illuminated and an inspection system having such an illumination device.

2. Description of the Related Art

Conventionally, photographing apparatuses such as video cameras and digital cameras are equipped with an illumination device that illuminates a subject to be photographed with light emitted from a light source when the brightness of the subject is insufficient. Such an illumination device has a light source and an optical element such as a reflecting mirror or a Fresnel lens that efficiently guides light beam emitted from the light source frontward (i.e. toward the subject to be photographed).

Various types of such illumination devices that are adapted to efficiently guide light beams emitted from the light source in variety of directions toward a subject to be photographed have been developed.

For example, Japanese Patent Application Laid-Open No. H04-138438 discloses an illumination device that illuminates an object to be illuminated with light beams emitted in the forward direction from the light source through a small prism having high condensing efficiency.

As another example, Japanese Patent Application Laid-Open No. H08-234277 (corresponding to U.S. Pat. No. 6,058,271) discloses an illumination device in which an optical member in the form of a light guide is provided in the vicinity of a light source to illuminate a surface to be illuminated with light beams emitted from the light source while condensing the light beams and making the distribution of light uniform without a significant light loss.

As another example, Japanese Patent Application Laid-Open No. H08-262537 (corresponding to U.S. Pat. No. 5,813,743) discloses an illumination device in which a prism is disposed in front of the light source in an inclined manner asymmetrically with respect to the optical axis of illumination in order to reduce the entire size of the apparatus.

On the other hand, Japanese Patent Application Laid-Open No. 2005-086391 and Japanese Patent Application Laid-Open No. 2004-177523 disclose illumination devices using a corner cube to effectively make use of light emitted from a light source that could otherwise go outside the illumination optical system.

In conventional illumination devices, a reflecting mirror is provided in rear of the light source (i.e. at the opposite side of the light source with respect to the object to be illuminated) to enhance the illumination efficiency.

In such illumination devices, if the positions of the light source and the reflecting mirror are displaced from the designed positions, the optical path of the light reflected by the reflecting mirror changes, which makes impossible to efficiently illuminate the object to be illuminated.

Japanese Patent Application Laid-Open No. 2004-177523 teaches to enhance the utilization efficiency of illumination light directed to an object to be illuminated by using a corner cube disposed in front of the light source (i.e. at the object-to-be-illuminated side of the light source).

However, in the arrangement disclosed in Japanese Patent Application Laid-Open No. 2004-177523, since the rotary parabolic mirror is provided in rear of the light source, highly accurate alignment of the light source and the rotary parabolic mirror is required, and misalignment therebetween will make it difficult to enhance the illumination efficiency.

SUMMARY OF THE INVENTION

An object of the present invention is to provide an illumination device that can efficiently illuminate an object to be illuminated without need for high precision in positioning.

An exemplary illumination device according to the present invention comprises a light source that supplies illumination light to an object to be illuminated and a corner cube member disposed at an opposite side of the light source with respect to the object to be illuminated. The corner cube member includes a plurality of corner cubes.

Further features of the present invention will become apparent from the following description of exemplary embodiments with reference to the attached drawings.

DESCRIPTION OF THE EMBODIMENTS

In the following, an exemplary embodiment of the illumination device according to the present invention will be described in detail with reference to the accompanying drawings.

Figure 1A:
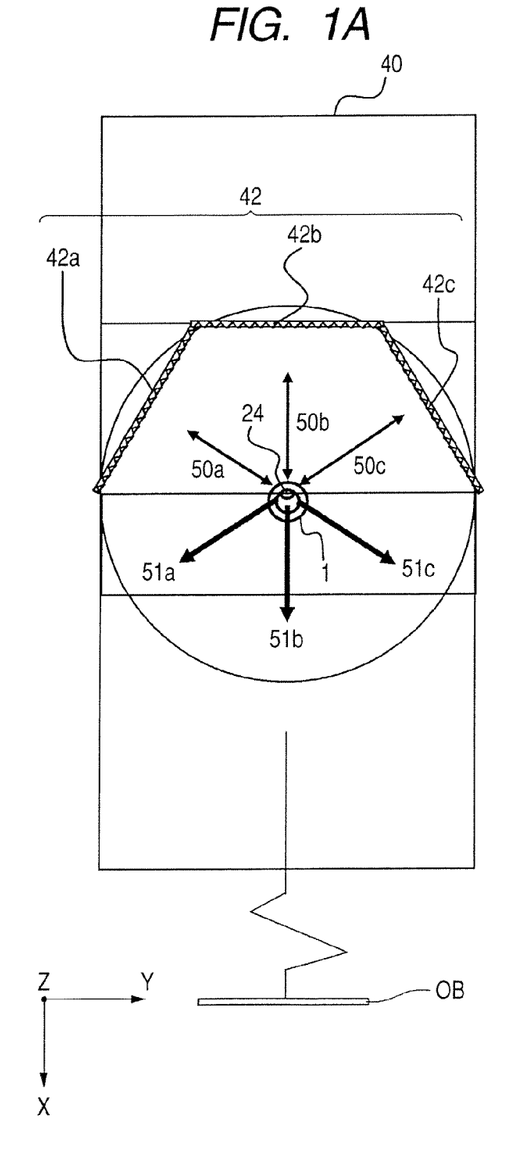
FIGS. 1A and 1B schematically show the general structure of an illumination device according to a first embodiment.
Figure 1B:
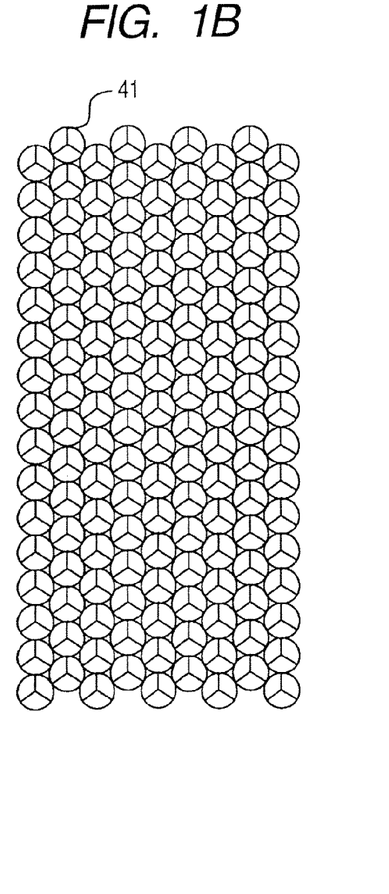

FIG. 1A is a cross sectional view of the relevant portion of an illumination device according to a first embodiment of the present invention. FIG. 1B illustrates a corner cube member which constitutes a part of the apparatus shown in FIG. 1A.

As shown in FIG. 1A, the illumination device (or lamp house) 40 has a light source 1 and a corner cube member 42 provided at the opposite side of the light source 1 with respect to the illumination direction.

The light source 1 is a xenon light emitting tube having a cylindrical shape extending in the direction perpendicular to the plane of the drawing sheet of FIG. 1A. The corner cube member 42 includes three corner cube sheets 42a to 42c.

The illumination device according to the first embodiment is adapted to illuminate an object to be illuminated OB with light that is emitted from the light source 1 and traveling directly toward the object to be illuminated OB and light that is emitted from the light source 1, reflected by the corner cube member 42, and then traveling toward the object to be illuminated OB.

As shown in FIG. 1A, light (or illumination light) emitted from the light source 1 diverges in all the directions. In FIG. 1A, while light beams 51a, 51b and 51c travel toward the object to be illuminated OB, light beams 50a, 50b and 50c directed away from the object to be illuminated OB travel toward corner cube sheets 42a, 42b and 42c.

Each of the corner cube sheets 42a, 42b, 42c has corner cubes 41 arranged periodically in two dimensional directions as shown in FIG. 1B.

The corner cube member 42 may has corner cubes arranged on a cylindrical inner surface.

Figure 2A:
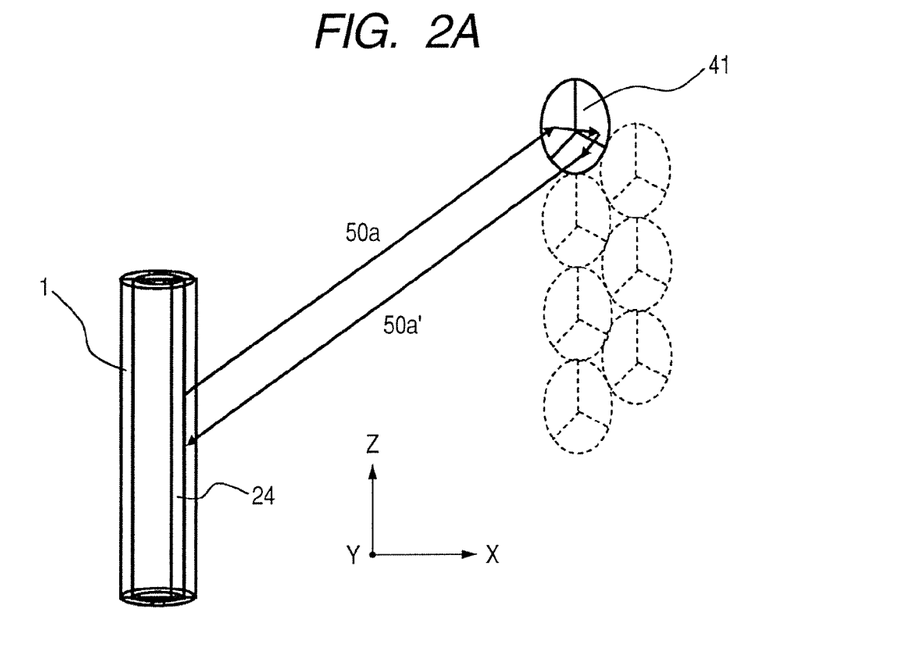
FIGS. 2A and 2B illustrate the optical path of light emitted from the light source and reflected by a corner cube in the first embodiment.
Figure 2B:
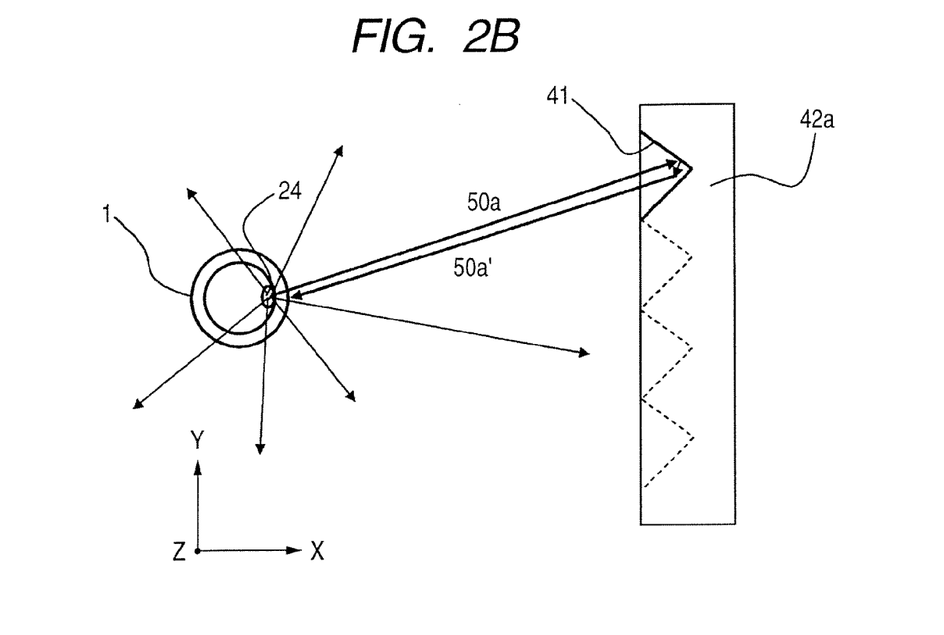

FIGS. 2A and 2B illustrate an optical path in the first embodiment.

In FIGS. 2A and 2B is shown an optical path 50a' of light 50a emitted from a light emitting area 24 of the light source 1 that is incident on and then reflected by a corner cube 41 and returns toward the light source 1.

The corner cube has a shape formed by cutting a corner of a cube. By its nature, the corner cube reflects light incident thereon back toward the direction from which the incident light comes. The light emerging from the corner cube travels on an optical path that is shifted or offset in a direction perpendicular to the direction of incidence depending on the position on the corner cube at which the light is incident. If the light incident surface of the corner cube is small, the shift amount is small. For example, the light incident on the corner cube with an offset of 1 mm from the center of the corner cube is reflected and emerging from the corner cube with a shift of 2 mm.

In the case where the size of the corner cube is 2 mm, the shift amount of the incident light is ±1 mm from the center of the corner cube at maximum. If the size of the light emitting area 24 of the light source 1 is approximately 2 mm in the XY cross section, the light reflected by the corner cube returns to the light source with a displacement of ±1 mm from the light emitting area 24. Therefore, the light source can function equivalently to a light source having an enlarged light emitting area.

In this embodiment, the corner cube member 42 is provided in one of regions partitioned by a plane containing the cylinder axis of the cylindrical light source 1.

With the use of the above described corner cube member 42 including the corner cube sheets 42a, 42b, 42c, light traveling in the direction opposite to the illumination direction is reflected by the corner cubes and travels also in the illumination direction. Consequently, divergent light emitted from the light source 1 can be utilized efficiently, and effective illumination light can be formed.

As described in the related art section, efficient use of divergent light emitted from the light source can also be made by using a reflecting mirror such as an elliptic mirror or a parabolic mirror. However, use of such a reflection mirror requires a high degree of precision in positioning the light source and the reflection mirror. For example, in the case of the elliptic mirror and the parabolic mirror, desired directivity is not achieved in some cases unless the light source is precisely positioned at the focal point of them.

In contrast, in the case where corner cube sheets 42a to 42c are provided by the light source 1, even if the set position of the corner cube sheets are displaced from the designed position to some extent, certain cubes, among the plurality of cubes in the corner cube sheets, that are different from intended cubes achieve the intended function. Thus, light beams traveling in the direction opposite to the illumination direction are returned toward the light source 1 and can be used as effective illumination beams. This means that the degree of precision in positioning the corner cube sheets 42a to 42c is not required to be high.

In the following, corner cubes and corner cube members that can be used in this embodiment will be described. Corner cubes having various outer shapes other than a circular shape (as seen from the front) like that shown in FIG. 1B can also be used.

FIGS. 3A, 3B, 3C and 3D schematically illustrate the shapes of corner cubes that can be used in this embodiment as seen from the front (the left drawings) and as seen from the side (the right drawings).

Figure 3A:
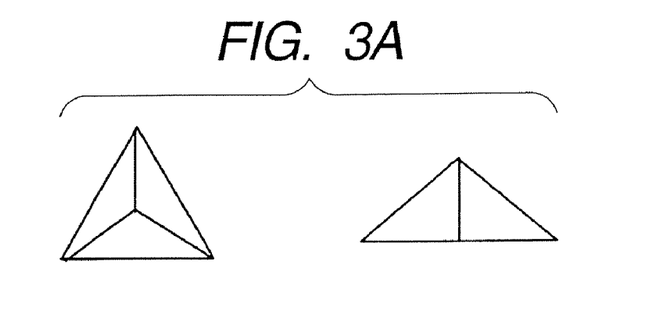
FIGS. 3A, 3B, 3C and 3D illustrate types of corner cubes having different shapes.

The corner cube shown in FIG. 3A has a regular triangular shape formed by simply cutting a corner of a cube. The corner cube shown in FIG. 3B has a shape formed by cutting the shape shown in FIG. 3A by the inscribed circle of the regular triangle in FIG. 3A along the direction perpendicular to the plane of the drawing sheet. The corner cube shown in FIG. 3C has a shape formed by cutting the shape shown in FIG. 3A to have a regular hexagonal shape having sides that are partially common to the sides of the regular triangle in FIG. 3A. The corner cube shown in FIG. 3C will be hereinafter referred to as the A-type regular hexagonal corner cube.

Figure 3B:
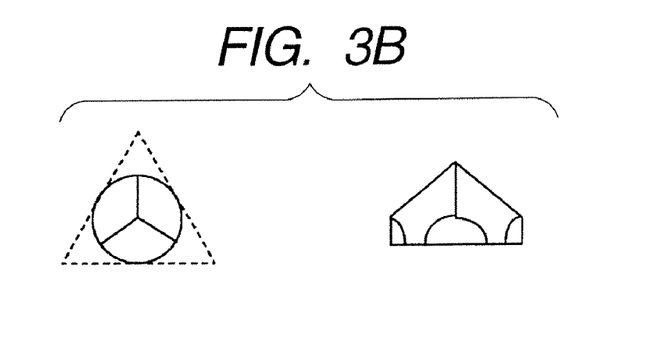
Figure 3C:
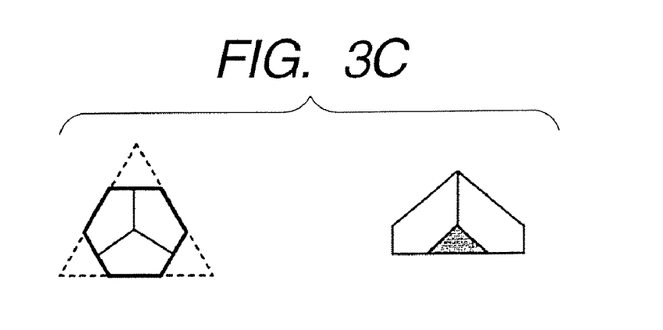
Figure 3D:
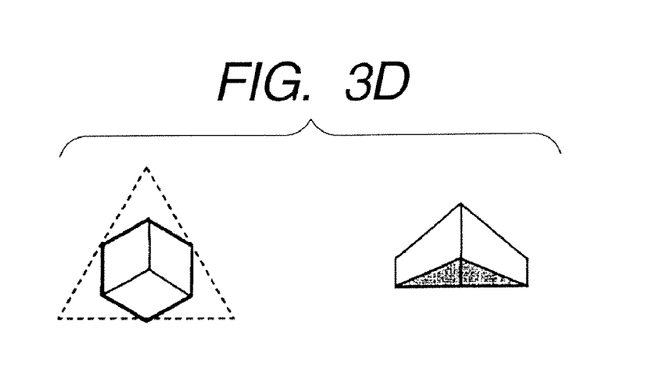

The corner cube shown in FIG. 3D has a shape formed by cutting the shape shown in FIG. 3A to have a regular hexagonal shape with apexes being on the sides of the regular triangle in FIG. 3A. The corner cube shown in FIG. 3D will be hereinafter referred to as the B-type regular hexagonal corner cube.

Figure 4A:
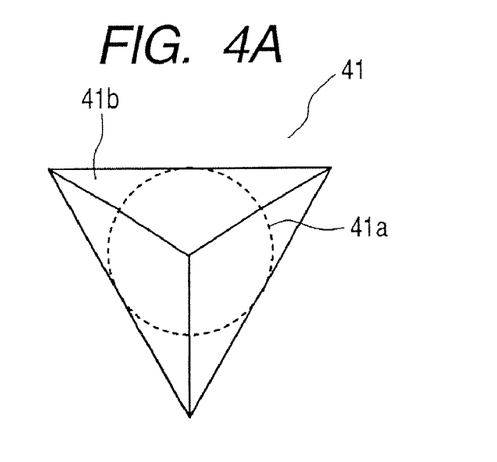
FIGS. 4A and 4B illustrate a corner cube having a regular triangular shape as seen from the front.

FIG. 4A schematically shows a corner cube 41 the same as that shown in FIG. 3A having a shape with a regular triangular outer contour formed by simply cutting a corner of a cube.

Figure 4B:
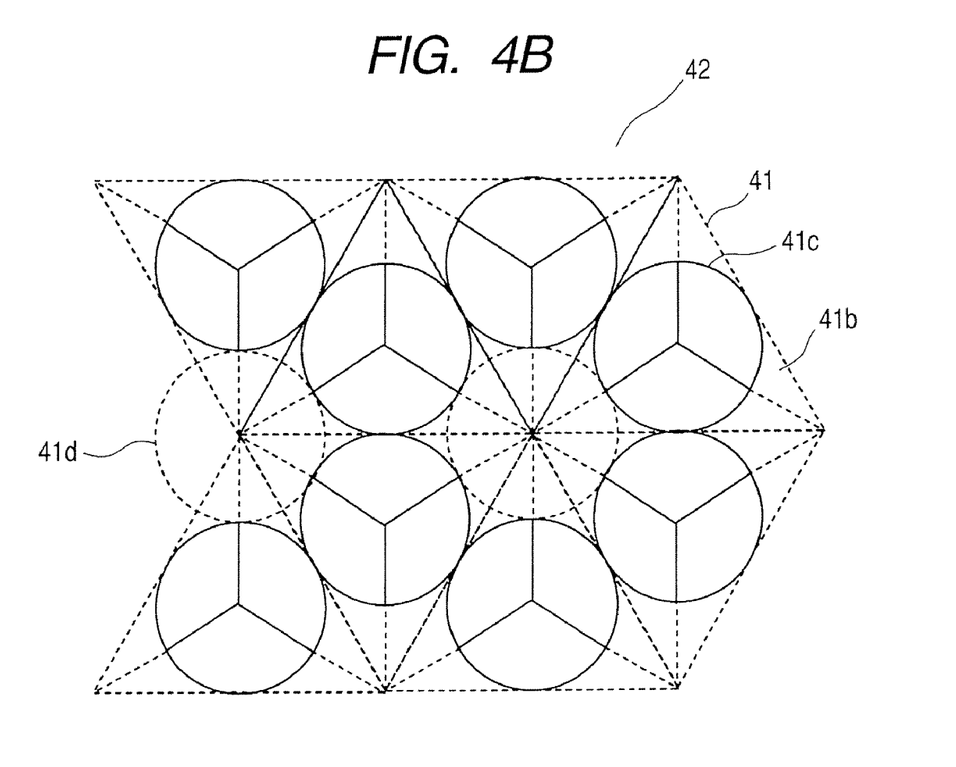

FIG. 4B schematically shows a corner cube member 42 in which corner cubes 41 formed by cutting in a regular triangular shape as shown in FIG. 4A are arranged in such a way that the centers of the corner cubes coincide with the apexes of regular hexagons arranged in a close-packed manner.

Light beams incident on the area of the corner cube inside the circle 41a indicated by the broken line in FIG. 4A from directions perpendicular to the plane of the drawing sheet are reflected by the corner cube to return in the direction opposite to the incident direction. Thus, the corner cube 41 functions effectively as a corner cube for the light beams incident on the area inside the circle 41a.

On the other hand, most of the light beams incident on the area 41b outside the circle 41a in FIG. 4A are not reflected toward the direction opposite to the incident direction. Thus, the corner cube 41 does not function as a corner cube for the light beams incident on the area outside the circle 41a.

Consequently, as shown in FIG. 4B, the areas inside the circles 41c indicated by solid lines are effective corner cube areas, but the areas inside the circles 41*d* indicated by broken lines are ineffective areas that do not function as corner cubes.

Figure 5:
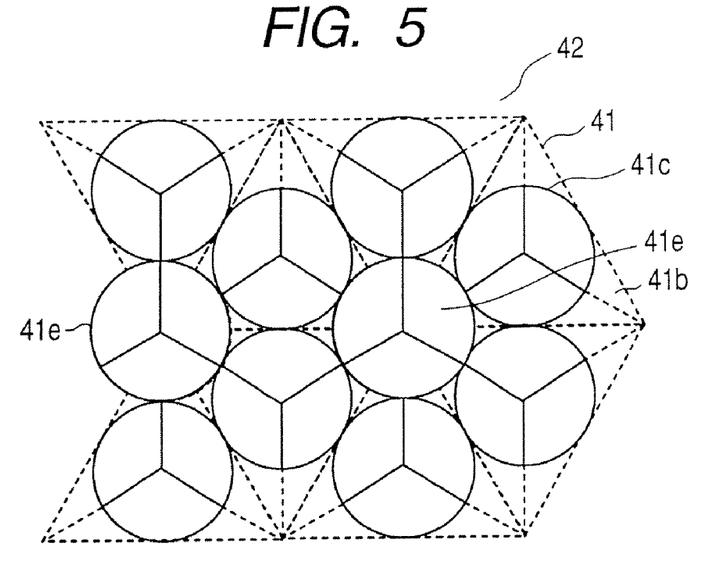
FIG. 5 illustrates a corner cube member in which corner cubes having a circular shape as seen from the front are closely arranged on a flat surface.

FIG. 5 schematically shows a corner cube member in which circular corner cubes 41*e* are arranged at the positions corresponding to the ineffective areas inside the circles 41*d* indicated by the broken lines in the corner cube member 42 shown in FIG. 4B with the centers of the corner cubes being at apexes of regular hexagons arranged in a close-packed manner. By arranging the corner cubes in a way as shown in FIG. 5, the effective area can be enlarged substantially all over the surface of the corner cube member 42.

Figure 6:
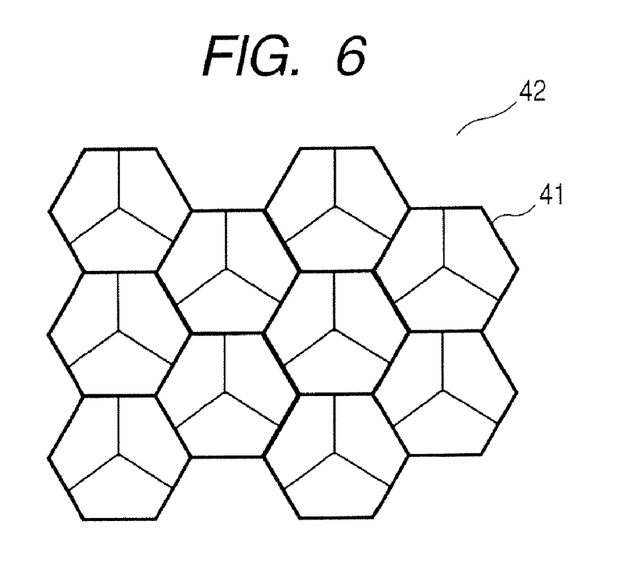
FIG. 6 illustrates a corner cube member in which corner cubes having a regular hexagonal shape as seen from the front are closely arranged on a flat surface.

FIG. 6 schematically shows a corner cube member 42 in which A-type regular hexagonal corner cubes 41 like that shown in FIG. 3C are arranged with no space therebetween with their centers being at the apexes of regular hexagons.

By arranging the corner cubes in a way as shown in FIG. 6, ineffective areas can be made small, and effective reflected light beams can be produced by the corner cube member.

Figure 7A:
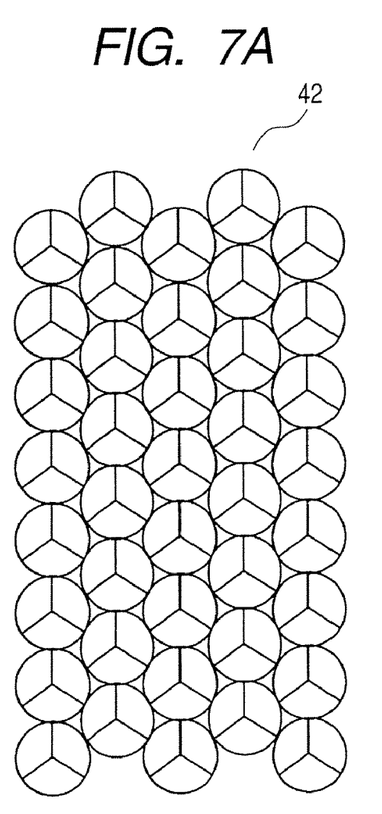
FIGS. 7A and 7B illustrate corner cube members in which corner cubes are arranged in the longitudinally long sheets.
Figure 7B:
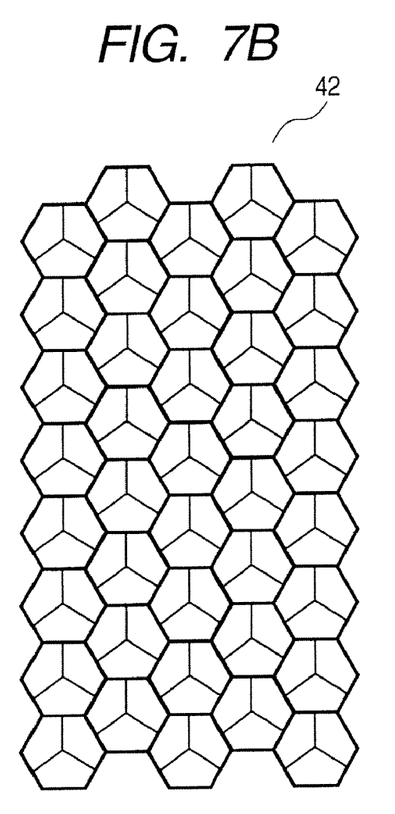

FIGS. 7A and 7B schematically show corner cube members in which corner cubes are arranged in the form of a longitudinally long sheet. FIG. 7A shows one in which circular corner cubes like that shown in FIG. 3B are arranged, and FIG. 7B shows one in which regular hexagonal corner cubes like that show in FIG. 3C are arranged.

Figure 8A:
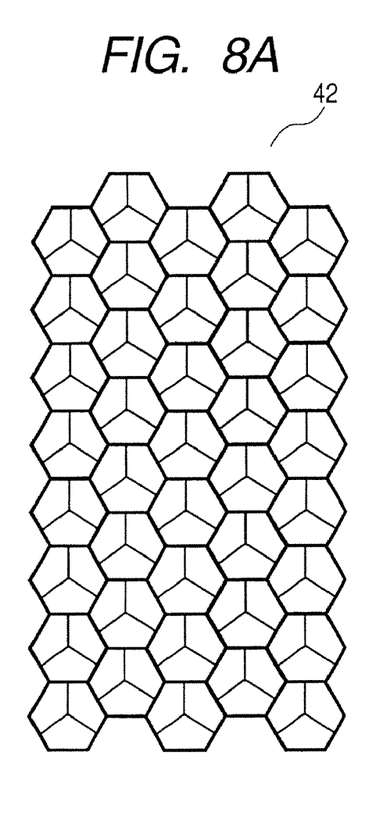
FIGS. 8A and 8B illustrate examples of arrangement of corner cubes in the corner cube member.
Figure 8B:
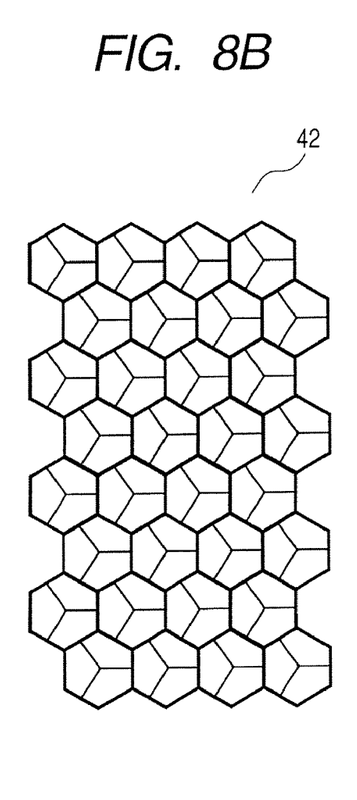

FIGS. 8A and 8B schematically show corner cube members 42 in which A-type regular hexagonal corner cubes like that shown in FIG. 3C that are regular hexagonal as seen from the front are arranged in the form of a sheet.

FIG. 8B shows a corner cube member 42 that is obtained by rotating the corner cube member 42 shown in FIG. 8A clockwise by 90 degrees within the plane of the drawing sheet.

Figure 9A:
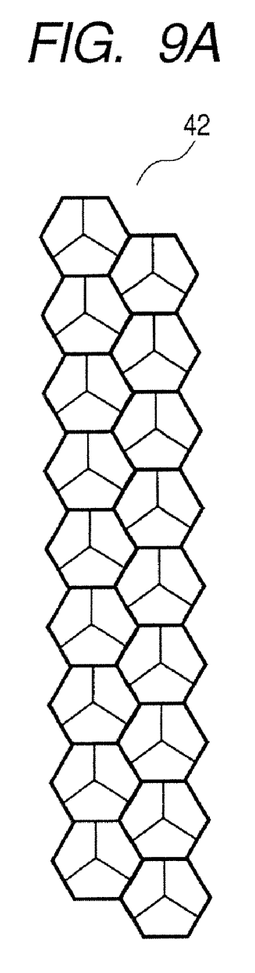
FIGS. 9A, 9B and 9C illustrate other examples of arrangement of corner cubes in the corner cube member.
Figure 9B:
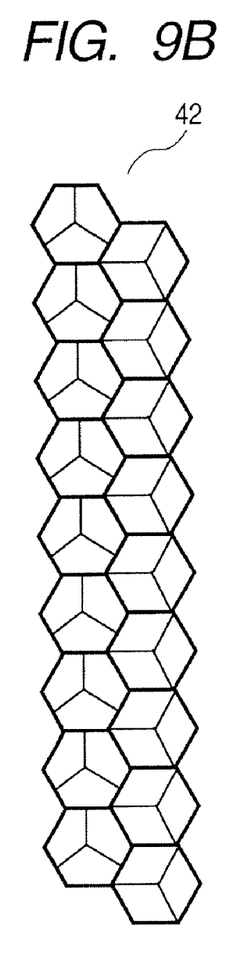
Figure 9C:
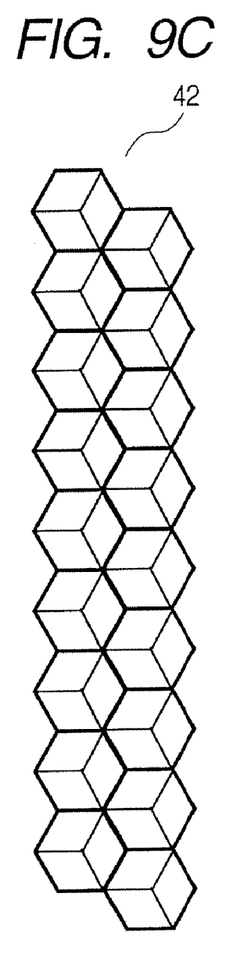

FIGS. 9A, 9B and 9C show ways of arranging corner cubes to produce a long and narrow corner cube member in which corner cubes having cutting orientations that are different from each other by 90 degrees are arranged. FIG. 9A shows one in which only A-type regular hexagonal corner cubes like that shown in FIG. 3C are arranged. FIG. 9B shows one in which A-type regular hexagonal corner cubes like that shown in FIG. 3C and B-type regular hexagonal corner cubes like that shown in FIG. 3D are mixed. FIG. 9C shows one in which only B-type regular hexagonal corner cubes like that shown in FIG. 3D are arranged.

Figure 10A:
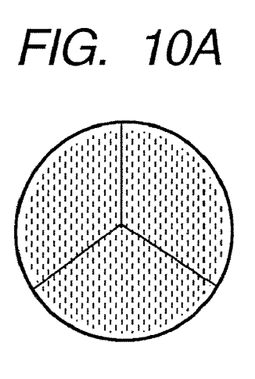
FIGS. 10A, 10B and 10C illustrate the effective area in relation to the angle of incidence on a corner cube having a circular shape as seen from the front.
Figure 10B:
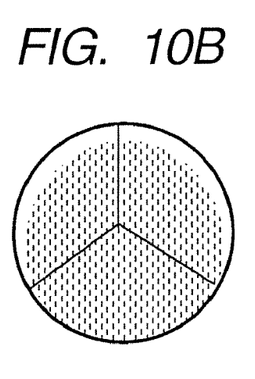
Figure 10C:
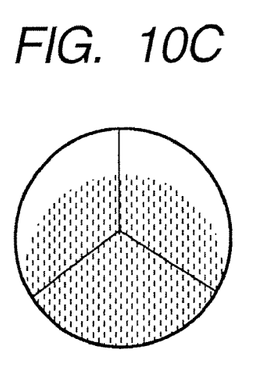

FIGS. 10A, 10B and 10C illustrate how the area of the effective returning light that have been incident on and reflected by a corner cube having a circular shape as seen from the front gradually decreases as the angle of incidence on the incident surface increases. FIG. 10A shows a case in which the light is incident on the corner cube vertically, FIG. 10B shows a case in which the light is incident on the corner cube obliquely at an angle of approximately 12 degrees, and FIG. 10C shows a case in which the light is incident on the corner cube obliquely at an angle of approximately 25 degrees. Even in the case of FIG. 10C where the angle of incidence is as large as 25 degrees, approximately 70% of the incident light returns and serves as effective light. The smaller the angle of incidence is made, the more the effective area is increased.

Figure 11A:
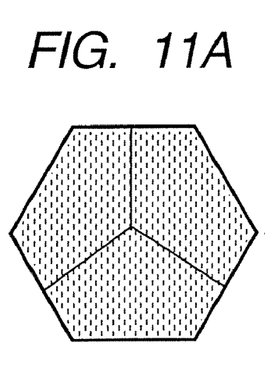
FIGS. 11A, 11B and 11C illustrate the effective area in relation to the angle of incidence on a corner cube having a regular hexagonal shape as seen from the front.
Figure 11B:
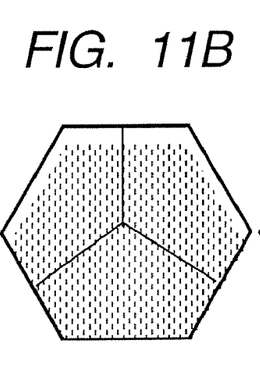
Figure 11C:
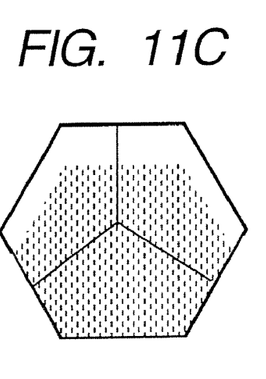

FIGS. 11A, 11B and 11C illustrate how the area of the effective returning light that have been incident on and reflected by a corner cube having a hexagonal shape as seen from the front gradually decreases as the angle of incidence on the incident surface increases.

FIG. 11A shows a case in which the light is incident on the corner cube vertically, FIG. 11B shows a case in which the light is incident on the corner cube obliquely at an angle of approximately 12 degrees, and FIG. 11C shows a case in which the light is incident on the corner cube obliquely at an angle of approximately 25 degrees.

As shown in FIGS. 11A, 11B and 11C, the incidence angle characteristics of the corner cube having a regular hexagonal shape as seen from the front are not greatly different from the characteristics of the circular corner cube shown in FIGS. 10A, 10B and 10C.

Figure 12:
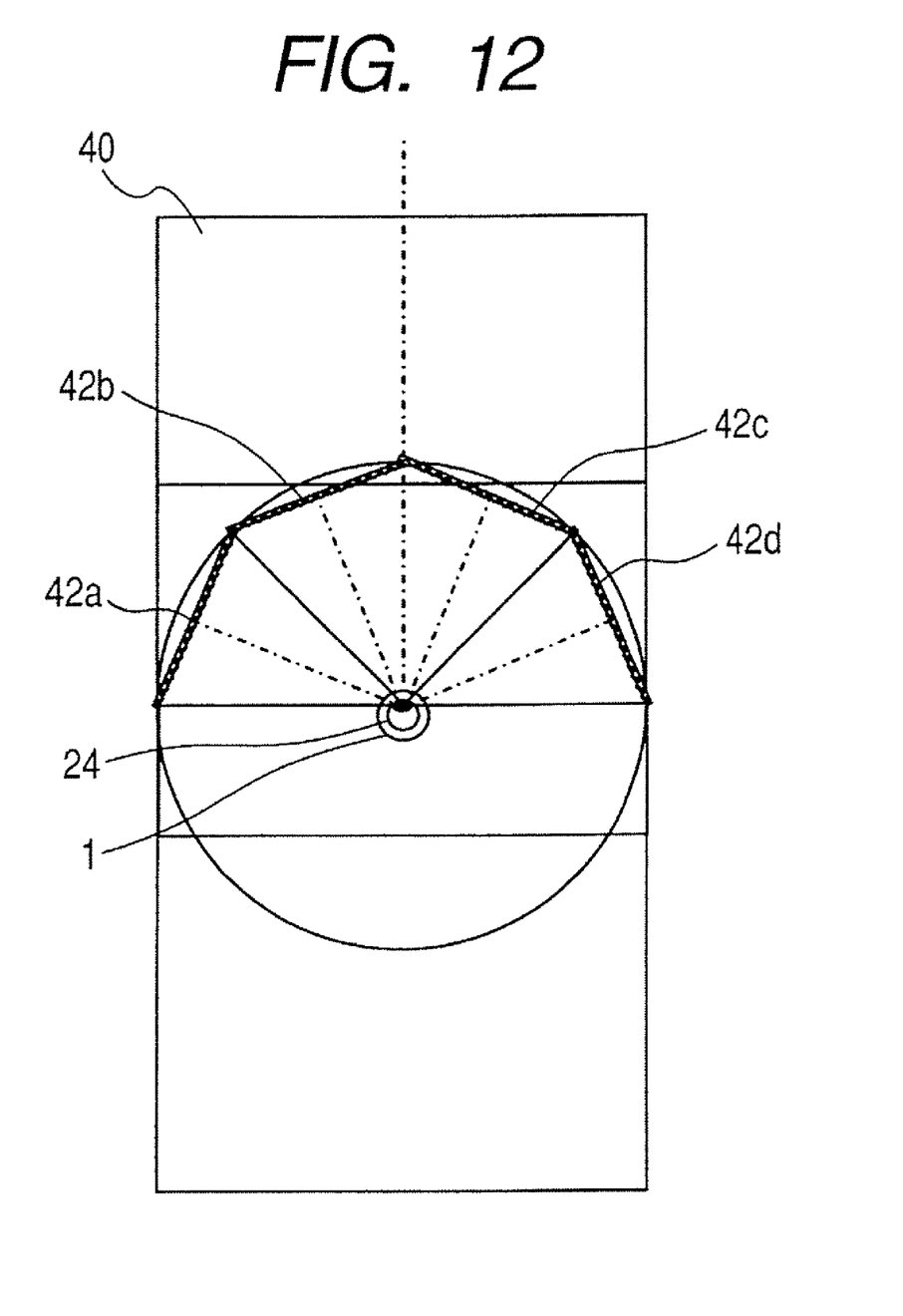
FIG. 12 schematically shows the general structure of an illumination device according to a second embodiment.

FIG. 12 is a cross sectional view of the relevant portion of an illumination device according to a second embodiment. The illumination device according to the second embodiment is designed in such a way that the maximum value of the angle of incidence of the light incident on the corner cubes in the corner cube sheets 42*a* to 42*d* from the light source 1 is 22.5 degrees.

The second embodiment differs from the first embodiment in that the corner cube sheets are divided into four segments in the radial cross section of the light emitting area 24.

Figure 13:
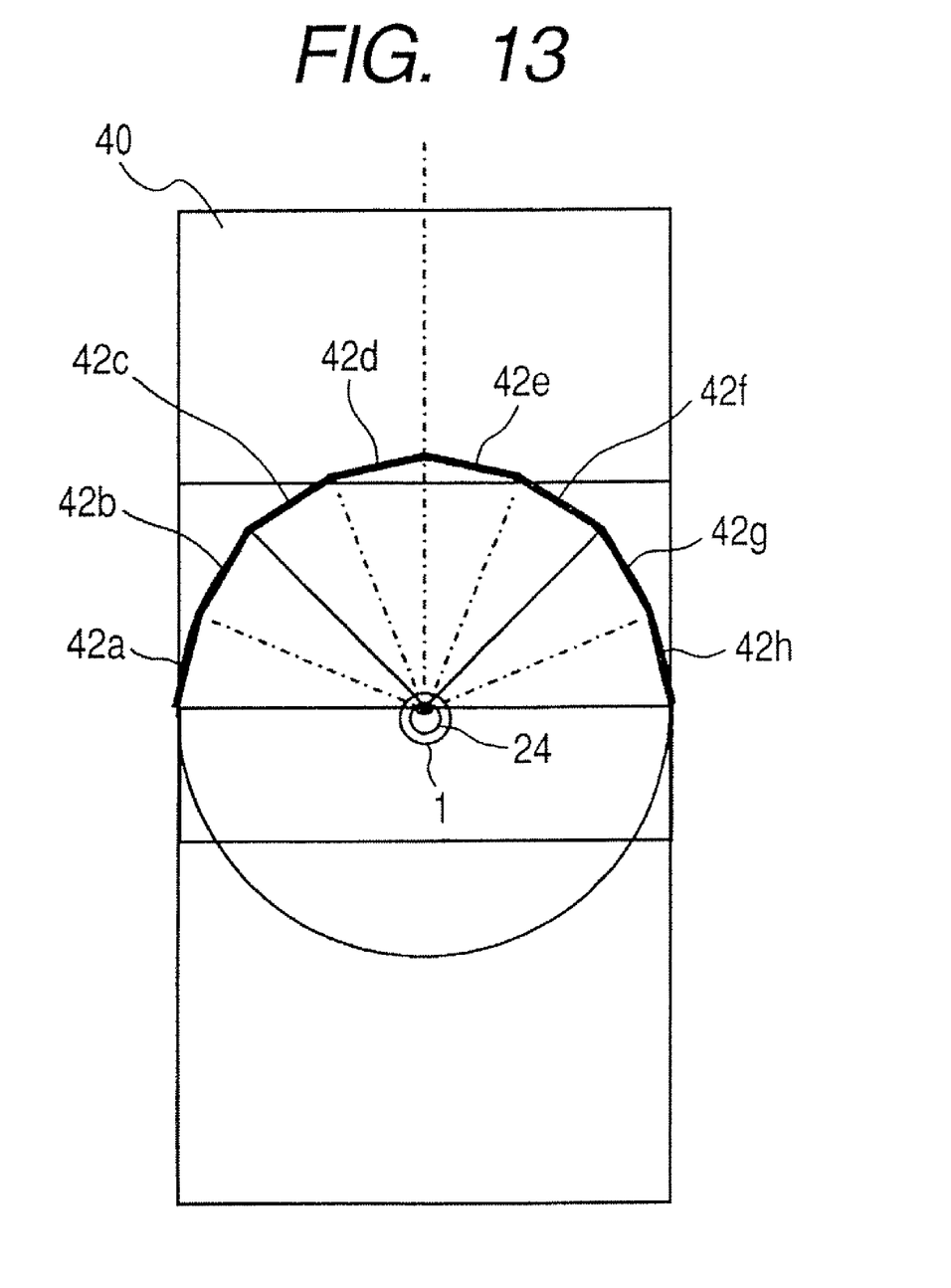
FIG. 13 schematically shows the general structure of an illumination device according to a third embodiment.

FIG. 13 is a cross sectional view of the relevant portion of an illumination device according to a third embodiment. The illumination device according to the third embodiment is designed in such a way that the maximum value of the angle of incidence of the light incident on the corner cubes in the corner cube sheets 42*a* to 42*d* from the light source 1 is 11.25 degrees. The third embodiment differs from the first embodiment in that the corner cube sheets are divided into eight segments in the radial cross section of the light emitting area 24.

As per the above, the number of division of the corner cube sheets in the illumination device according to the embodiments may as well be determined by appropriately taking into account the maximum angle of incidence of the light incident on the corner cubes. In any case, it is preferred that the number of division be not smaller than three.

Figure 14A:
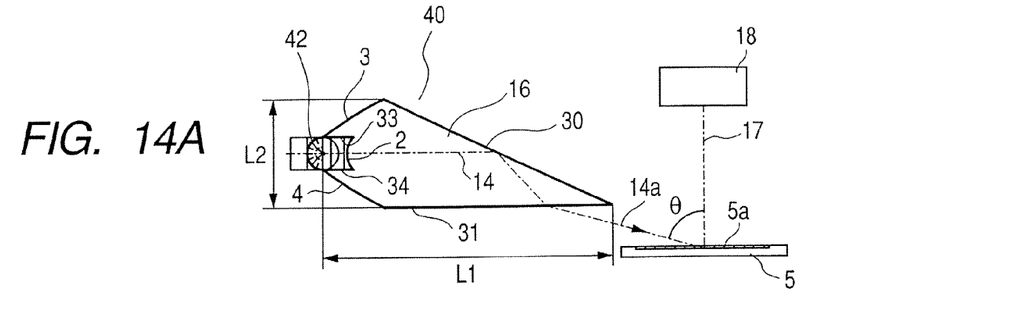
FIGS. 14A and 14B schematically show the general structure of an inspection system equipped with an illumination device according to the present invention.
Figure 14B:
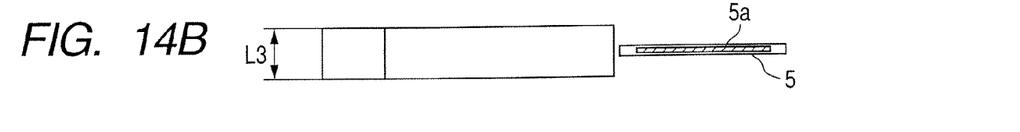
Figure 15:
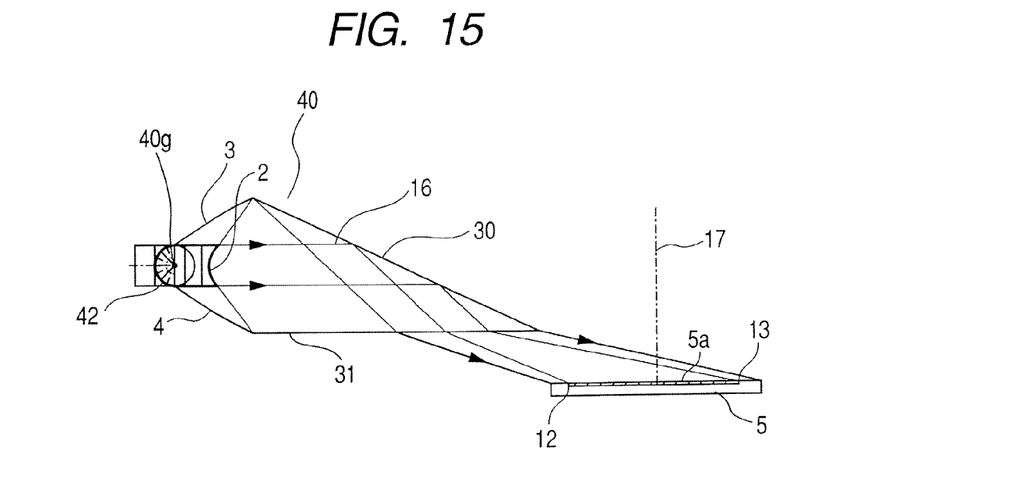
FIG. 15 is an optical path diagram of the inspection system equipped with an illumination device according to the present invention.

In the following, an inspection system equipped with an illumination device according to the present invention will be described with reference to FIGS. 14A, 14B and 15. FIG. 14A is a schematic side view of an inspection system according to this embodiment. FIG. 14B is a schematic top view of the inspection system. FIG. 15 is an optical path diagram drawn by ray tracing for illumination light from the illumination device 40 in the inspection system according to this embodiment.

The illumination device according to this embodiment has a prism member 16 disposed at the opposite side of the light source 1 with respect to the side at which the corner cube member 42 is disposed. (In other words, the prism member 16 is disposed at the same side of the light source 1 as the side at which an object to be illuminated is present.)

The inspection system according to this embodiment illuminates an object to be illuminated 5 with light beams emerging from the prism member 16 of the illumination device with directivity toward an oblique direction inclined at a large angle.

The prism member 16 has a first light incident surface 2 having a positive refractive power on which illumination light from the light source 1 and the corner cube member 42 is incident, a second light incident surfaces 33, 34 in the form of flat surfaces parallel to the optical axis of the first light incident surface 2 and a second reflection surfaces 3, 4 having curvature. The prism member 16 further has a first reflection surface in the form of a flat surface and a light emitting surface 31 in the form of a flat surface.

The first light incident surface 2 may be a flat surface. In that case, the second light incident surfaces 33, 34 are perpendicular to the first light incident surface 2. In this embodiment, the first light incident surface 2 and the second light incident surfaces 33, 34 are different surfaces.

The illumination device 40 has an illumination axis 14 that coincides with the center axis (i.e. the axis including the center of curvature of the light incident surface 2) of the illumination device. Light on the illumination axis 14 is indicated by reference sign 14a.

In the following, the structure of the prism 16 used in this embodiment will be described. The light beam 14a on the illumination axis 14 of the illumination system is emitted from the light emitting surface 31 of the prism 16 and incident on an illumination area 5a of the object to be illuminated 5 at an angle of incidence indicated by θ. In FIGS. 14A and 15, a normal line of the illumination area 5a of the object to be illuminated 5 is indicated by alternate long and short dash line 17.

A photographing apparatus 18 is disposed in such a way that its axis is in alignment with the normal line 17.

In FIGS. 14A, 14B and 15, the light emitted from the illumination device 40 and incident on the light incident surface 2 is reflected by the reflection surface 30 and emitted from the light emitting surface 31 to illuminate the object to be illuminated 5.

On the other hand, the light incident on the light incident surface 33 is reflected by the reflection surface 3 and the reflection surface 30 and emitted from the light emitting surface 31 to illuminate the object to be illuminated 5.

The light incident on the light incident surface 34 is reflected by the reflection surface 4 and the reflection surface 30 and emitted from the light emitting surface 31 to illuminate the object to be illuminated 5.

Each of the reflection surfaces 3, 4 and 30 of the prism 16 is a reflective surface provided with a metal film or a total reflection surface configured to satisfy the total reflection condition.

The prism 16 used in this embodiment is made of acrylic. The object to be illuminated 5 has a rod-like shape (or cylindrical shape) with a length of 300 mm, and the illumination area 5a with a length of 200 mm is uniformly illuminated.

The horizontal dimension L1 of the prism 16 indicated in FIG. 14A is approximately 550 mm, the vertical dimension L2 thereof is approximately 200 mm, the thickness L3 shown in FIG. 14B is approximately 100 mm. The angle of incidence θ is designed to be 75 degrees at the center.

FIG. 15 illustrates a situation in which the entire illumination area 5a of the object to be illuminated 5 is illuminated with scattered light beams emitted from the light emitting point 40g, among the light emitting points of the illumination device 40, that is remotest from the light incident surface 2 on the illumination axis 14 of the illumination system.

FIG. 15 shows optical paths of the light beams, among the light beams emitted from the illumination device 40, that are emitted from the light source 1 and incident on the light incidence surfaces 2, 33, 34 of the prism 16.

When a corner cube member according to any one of the above described embodiments is used, the light beams having been reflected by the corner cubes travel on substantially the same optical paths as the light beams emitted from the light emitting tube.

Consequently, efficient illumination of the object to be illuminated 5 can be achieved.

According to this embodiment, the small illumination area 5a of the object to be illuminated 5 can be uniformly illuminated from an oblique direction easily. Image information of the illumination area 5a of the object to be illuminated 5 may be picked up by the photographing apparatus 18. In this way, an inspection system that can detect, with high accuracy, image information of the illumination area 5a that is uniformly illuminated can be built.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2006-270652 filed Oct. 2, 2006, which is hereby incorporated by reference herein in its entirety.

What is claimed is:

1. An illumination device comprising:
    a light source that supplies illumination light to an object to be illuminated;
    a corner cube member comprising a plurality of sheets of corner cubes, the sheets being arranged next to each other and facing different directions, at least one of the sheets being disposed entirely behind the light source with respect to the object to be illuminated, and each of the sheets of the corner cube member including a plurality of corner cubes; and
    a prism member that guides light from the light source to the object to be illuminated, the prism member being disposed at an opposite side of the light source with respect to the corner cube member, the prism member having a first light incident surface on which light from the light source is incident, a second light incident surface formed as a surface different from the first light incident surface, a first reflecting surface that reflects light incident on the first light incident surface, a second reflecting surface that reflects light incident from the second light incident surface toward the first light reflecting surface and a light emitting surface that emits light reflected by the first reflecting surface.

2. An illumination device according to claim 1, wherein the plurality of corner cubes in each sheet is arranged in such a way that the center of each corner cube is located at an apex of regular hexagons that are arranged in a close-packed manner.

3. An illumination device according to claim 1, wherein each of the plurality of corner cubes has a front-facing circular shape.

4. An illumination device according to claim 1, wherein each of the plurality of corner cubes has a front-facing regular triangular shape.

5. An illumination device according to claim 1, wherein each of the plurality of corner cubes, as seen from the front with respect to the light source, is regular hexagonal.

6. An illumination device according to claim 1, wherein the light source is a light emitting tube having a cylindrical shape, and the corner cube member is disposed in one of regions partitioned by a plane that contains the cylinder axis of the cylindrical shape.

7. An illumination system comprising:
    an illumination device according to claim 1 that illuminates an object to be illuminated having a cylindrical shape with light; and
    a photographing apparatus that picks up image information of the object to be illuminated that is illuminated by the illumination device.

* * * * *